(12) United States Patent
Liu et al.

(10) Patent No.: US 10,653,302 B2
(45) Date of Patent: May 19, 2020

(54) RIGID ENDOSCOPE

(71) Applicant: BEIJING WESTON ASIA-PACIFIC OPTO-ELECTRIC INSTRUMENT CO., LTD., Beijing (CN)

(72) Inventors: Xiaohua Liu, Beijing (CN); Ye Yuan, Beijing (CN); Dewen Cheng, Beijing (CN); Liquan Dong, Beijing (CN); Xiatian Wang, Beijing (CN)

(73) Assignee: BEIJING WESTON ASIA-PACIFIC OPTO-ELECTRIC INSTRUMENT CO., LTD., Beijing (CN)

( * ) Notice: Subject to any disclaimer, the term of this patent is extended or adjusted under 35 U.S.C. 154(b) by 0 days.

(21) Appl. No.: 15/745,937

(22) PCT Filed: Sep. 23, 2015

(86) PCT No.: PCT/CN2015/090393
§ 371 (c)(1),
(2) Date: Jan. 18, 2018

(87) PCT Pub. No.: WO2017/012192
PCT Pub. Date: Jan. 26, 2017

(65) Prior Publication Data
US 2018/0206702 A1   Jul. 26, 2018

(30) Foreign Application Priority Data

Jul. 22, 2015   (CN) .................... 2015 2 0532348 U

(51) Int. Cl.
*A61B 1/002* (2006.01)
*G02B 23/24* (2006.01)
*A61B 1/06* (2006.01)

(52) U.S. Cl.
CPC ................ *A61B 1/002* (2013.01); *A61B 1/06* (2013.01); *A61B 1/0684* (2013.01); *G02B 23/24* (2013.01);
(Continued)

(58) Field of Classification Search
None
See application file for complete search history.

(56) References Cited

U.S. PATENT DOCUMENTS 4,964,710 A     10/1990   Leiner
5,188,092 A *   2/1993    White ................ A61B 1/00103
                                                      359/435
(Continued)

FOREIGN PATENT DOCUMENTS

CN     201000508     1/2008
CN     201091570     7/2008
(Continued)

OTHER PUBLICATIONS

International Search Report issued in the corresponding PCT application No. PCT/CN2015/090393, dated Apr. 28, 2016, 6 pages.
(Continued)

*Primary Examiner* — Derek S. Chapel
(74) *Attorney, Agent, or Firm* — Hamre, Schumann, Mueller & Larson, P.C.

(57) ABSTRACT

A rigid endoscope includes an endoscope tube, a light-emitting diode (LED) chip, an objective lens group, a rod lens group and a lead. the objective lens group and the rod lens group are disposed in the endoscope tube and arranged in a direction from a front end to a rear end of the endoscope tube; the LED chip is mounted at the front end of the endoscope tube; and the lead is led out from the LED chip, runs through a gap between an inner circle of the endoscope
(Continued)

tube and an outer circle of the objective lens group, and arrives at the rear end of the endoscope tube.

15 Claims, 4 Drawing Sheets

(52) U.S. Cl.
CPC ....... *G02B 23/243* (2013.01); *G02B 23/2461* (2013.01)

(56) References Cited

U.S. PATENT DOCUMENTS

| | | | |
|---|---|---|---|
| 2001/0007051 A1* | 7/2001 | Nakashima | A61B 1/05 600/179 |
| 2006/0069314 A1* | 3/2006 | Farr | A61B 1/00096 600/179 |
| 2008/0027276 A1* | 1/2008 | Rovegno | A61B 1/0676 600/109 |

FOREIGN PATENT DOCUMENTS

| | | | |
|---|---|---|---|
| CN | 203720449 | | 7/2014 |
| CN | 203720449 U | * | 7/2014 |
| CN | 203736154 | | 7/2014 |
| CN | 203736154 U | * | 7/2014 |
| CN | 203745727 | | 7/2014 |
| CN | 104873164 | | 9/2015 |
| CN | 104880815 | | 9/2015 |
| CN | 104880816 | | 9/2015 |
| JP | 2005-224385 | | 8/2005 |
| WO | WO-2008016195 A1 | * | 2/2008 ............. A61B 1/041 |

OTHER PUBLICATIONS

Extended European Search Report, issued in the corresponding European patent application No. 15898748.7, dated Feb. 19, 2019, 7 pages.

* cited by examiner

RIGID ENDOSCOPE

TECHNICAL FIELD

The present disclosure relates to a rigid endoscope.

BACKGROUND

Endoscope not only can be used as a medical optical instrument for diagnosis and treat but also can be used as industrial testing equipment, and has more than two hundred years of history. Although fiberscopes, electronic endoscopes, capsule endoscopes and ultrasound electronic endoscopes are now available, medical and industrial rigid endoscopes are still widely applied due to the advantages of excellent image quality, convenience for minimally invasive surgery, considerably lower price than soft endoscopes, and high temperature and pressure sterilization. However, relatively speaking, the rigid endoscope has too high price and poor imaging quality, is difficult to be widely popularized in outpatient examination, and hence will result in the etiological diagnosis delay of patients or even misdiagnosis.

SUMMARY

The embodiment of the present invention provides a rigid endoscope, which can greatly improve the imaging resolution due to adoption of single-tube design, can increase the lighting angle and improve the uniformity due to adoption of LED chip for illumination, and can significantly improve the image quality and greatly reduce the cost due to adoption of free curved surface design and one-time die casting of all the lenses.

Some embodiments of the present invention provide a rigid endoscope, which comprises: an endoscope tube, a LED chip, an objective lens group, a rod lens group and a lead, wherein the objective lens group and the rod lens group are disposed in the endoscope tube and arranged in a direction from the front end to the rear end of the endoscope tube; the LED chip is mounted at the front end of the endoscope tube; and the lead is led out from the LED chip, runs through a gap between an inner circle of the endoscope tube and an outer circle of the objective lens group, and arrives at the rear end of the endoscope tube.

In some examples, the rigid endoscope further comprises a main endoscope body and an eyepiece group; the rear end of the endoscope tube is connected to the main endoscope body; the eyepiece group is disposed in the endoscope tube and at the rear end of the rod lens group; or the eyepiece group is disposed in the main endoscope body.

In some examples, the LED chips are mounted in a gap between an inner circle of the endoscope tube and an outer circle of the objective lens group.

In some examples, the LED chip is disposed at the edge of the front end of the objective lens group and is close to the inner wall of the endoscope tube.

In some examples, the objective lens group includes a first objective lens and a second objective lens; the first objective lens and the second objective lens are sequentially arranged in a direction from the front end to the rear end of the endoscope tube; and the LED chip is mounted between the first objective lens and the second objective lens and disposed at the edge of the rear end of the first objective lens.

In some examples, the first objective lens includes a central portion, of which the rear end surface is set to be a concave surface, and an edge portion disposed at the periphery of the central portion; and the rear end surface of the edge portion is a curved surface or a plane, so that light emitted from the LED chips can propagate towards the front end and stray light can be suppressed.

In some examples, the rear end surface of the edge portion of the first objective lens is a curved surface protruded towards the rear end of the endoscope tube.

In some examples, the front end surface of the first objective lens is a plane; and the first objective lens is taken as a forefront protection plate of the rigid endoscope.

In some examples, the LED chip includes a chip which is designed to be annular or a plurality of LED chips arranged in an annular shape or a chip set disposed on a flexible material.

In some examples, the lenses of at least one of the objective lens group, the rod lens group or the eyepiece group adopt aspheric lens design and have roughly equal diameter.

In some examples, all of the objective lens group, the rod lens group and the eyepiece group adopt die cast lenses.

In some examples, the endoscope tube and the main endoscope body adopt detachable assembled connection structure or inseparable integral structure.

In some examples, the LED chip is a white-light LED chip.

In some examples, the ultrahigh-image-quality rigid endoscope further comprises a power supply channel running through the tube wall of the main endoscope body and the endoscope tube; and the rear end of the lead is led out from the power supply channel to the outside of the main endoscope body.

In some examples, the material of the endoscope tube is stainless steel.

In some examples, the objective lens group, the rod lens group, the eyepiece group, the LED chip and the lead are sealed into the endoscope tube.

In some examples, the rigid endoscope is a single-tube rigid endoscope.

In some examples, the objective lens group, the rod lens group and the eyepiece group form an imaging system of the rigid endoscope.

Some other embodiments of the present invention provide a rigid endoscope, which comprises: an endoscope tube, an objective lens group and a rod lens group, wherein the objective lens group and the rod lens group are disposed in the endoscope tube and arranged in a direction from the front end to the rear end of the endoscope tube; and at least one of the objective lens group or the rod lens group adopts die cast lenses.

In some examples, the rigid endoscope further comprises a main endoscope body and an eyepiece group; the rear end of the endoscope tube is connected to the main endoscope body; the eyepiece group is disposed in the endoscope tube and at the rear end of the rod lens group; or the eyepiece group is disposed in the main endoscope body.

In some examples, the eyepiece group adopts die cast lens.

In some examples, the lenses in at least one of the objective lens group, the rod lens group or the eyepiece group adopt aspheric lens design.

In some examples, the rod lens group is an integral optical element.

Some other embodiments of the present invention further provide a rigid endoscope, which comprises: an endoscope tube, an objective lens group, a rod lens group and an eyepiece group, wherein the objective lens group, the rod lens group and the eyepiece group are sequentially arranged in the endoscope tube in a direction from the front end to the rear end of the endoscope tube; and at least one of the objective lens group, the rod lens group or the eyepiece group adopts die cast lens.

In some examples, the lenses in at least one of the objective lens group, the rod lens group or the eyepiece group adopt aspheric lens design.

BRIEF DESCRIPTION OF THE DRAWINGS

Simple description will be given below to the accompanying drawings of the embodiments to provide a more clear understanding of the technical proposals of the embodiments of the present invention. Obviously, the drawings described below only involve some embodiments of the present invention but are not intended to limit the present invention.

Figure 1:
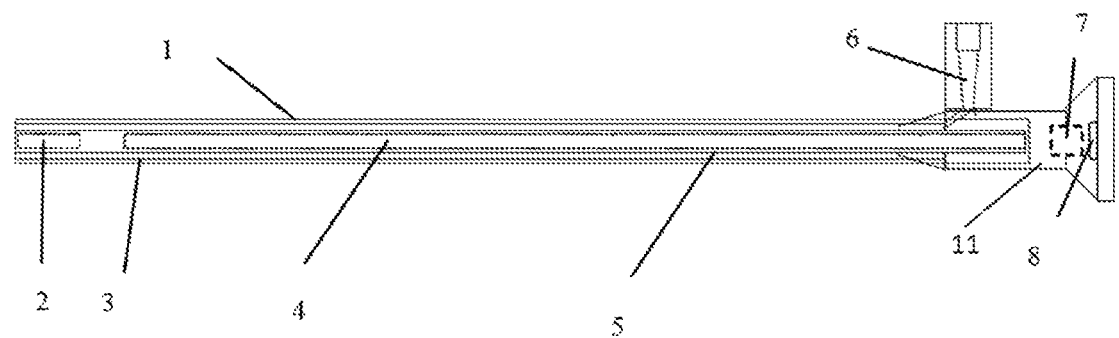
FIG. 1 is a schematic structural sectional view of a double-tube rigid endoscope.

Reference numerals of the accompanying drawings: 1—outer endoscope tube, 2—objective lens group, 3—optical fiber, 4—rod lens group, 5—inner endoscope tube, 6—light cone, 7—eyepiece group, 8—rear protection plate, 10—endoscope tube, 20—objective lens group, 50—spacer, 40—rod lens group, 70—eyepiece group, 90—LED chip, 15—lead, 12—main endoscope body, 14—eyeshade, 13—power supply channel.

DETAILED DESCRIPTION

For more clear understanding of the objectives, technical proposals and advantages of the embodiments of the present invention, clear and complete description will be given below to the technical proposals of the embodiments of the present invention with reference to the accompanying drawings of the embodiments of the present invention. Obviously, the preferred embodiments are only partial embodiments of the present invention but not all the embodiments. All the other embodiments obtained by those skilled in the art without creative efforts on the basis of the embodiments of the present invention illustrated shall fall within the scope of protection of the present invention.

The present disclosure provides a rigid endoscope. The rigid endoscope may be manufactured into a detachable optical rigid endoscope (hard tube endoscope). When an endoscope tube and a main endoscope body adopt detachable design, the endoscope tube becomes disposable consumable, and image adjustment is not required on site, so the rigid endoscope can be more conveniently used. In addition, as the endoscope tube becomes disposable consumable, cross-infection can be avoided, and popularization can be more favorable.

FIG. 1 is a sectional view of a double-tube rigid endoscope taken along the axial direction. The rigid endoscope comprises an endoscope tube including an inner endoscope tube 5 and an outer endoscope tube 1, an optical fiber 3, an objective lens group 2, a rod lens group 4, an eyepiece group 7, a light cone 6, a main endoscope body 11 and a rear protection plate 8. The optical fiber 3 is disposed between the inner endoscope tube 5 and the outer endoscope tube 1; the rear end of the optical fiber 3 is in butted joint to a light outlet of the light cone 6; and the front end of the optical fiber 3 is extended to the front end of the endoscope tube and used for lighting.

The endoscope tube of the double-tube rigid endoscope as shown in FIG. 1 includes an inner tube and an outer tube. The single-tube design can be difficult to be realized mainly due to the fact that the optical fiber for lighting cannot be simultaneously assembled into a single endoscope tube together with an imaging system. A new lighting method is required for the traditional inseparable rigid endoscope to realize the novel single-tube design. Meanwhile, when applied in a detachable rigid endoscope (namely an endoscope tube and a main endoscope body can be detachable from each other), as the objective lens group and the rod lens group are mounted in the inner endoscope tube but the eyepiece group is mounted in the main endoscope body, on-site assembly is required upon being used, so the on-site image adjustment of the imaging system cannot be realized, and hence images may be blurred. Therefore, the endoscope tube and the main endoscope body can be difficult to be separated in the traditional rigid endoscope. In addition, the cost of the objective lens group, the rod lens group and the eyepiece group manufactured by the traditional method is too high, resulting in large resource waste if it is disposable in one time.

Figure 2:
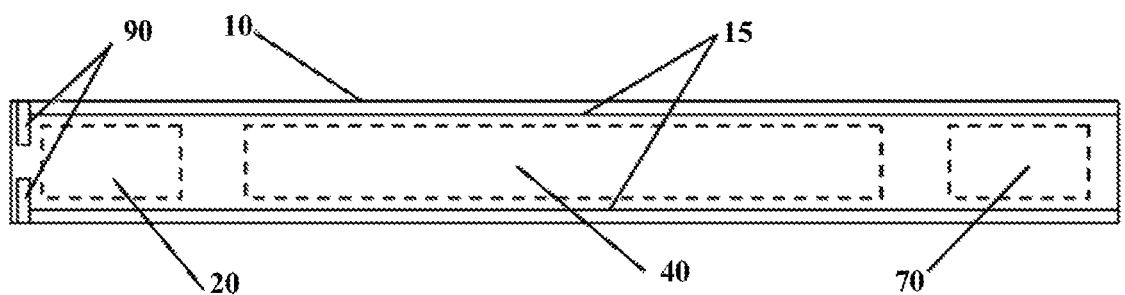
FIG. 2 is a schematic structural sectional view of an endoscope tube part of the rigid endoscope provided by some embodiments of the present invention.
Figure 3:
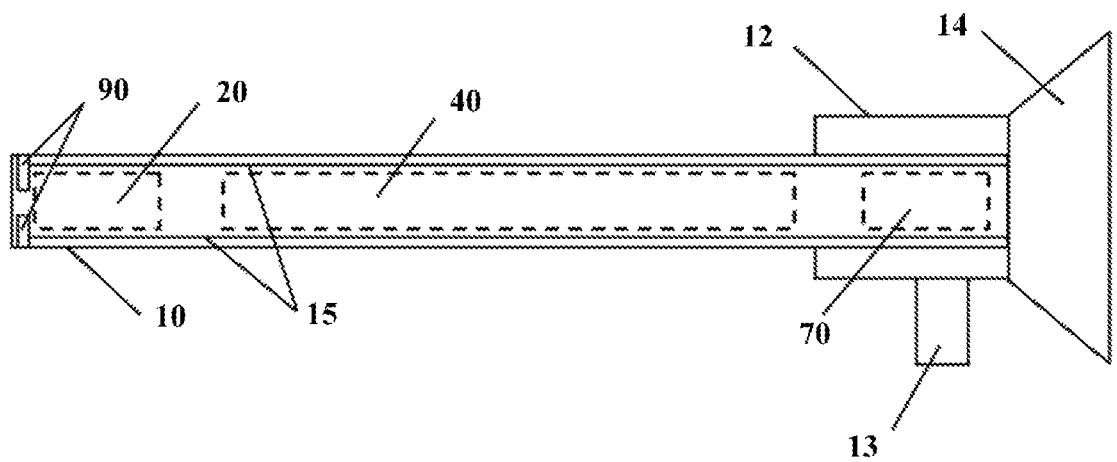
FIG. 3 is a schematic structural sectional view of a detachable rigid endoscope provided by some embodiments of the present invention.
Figure 4:
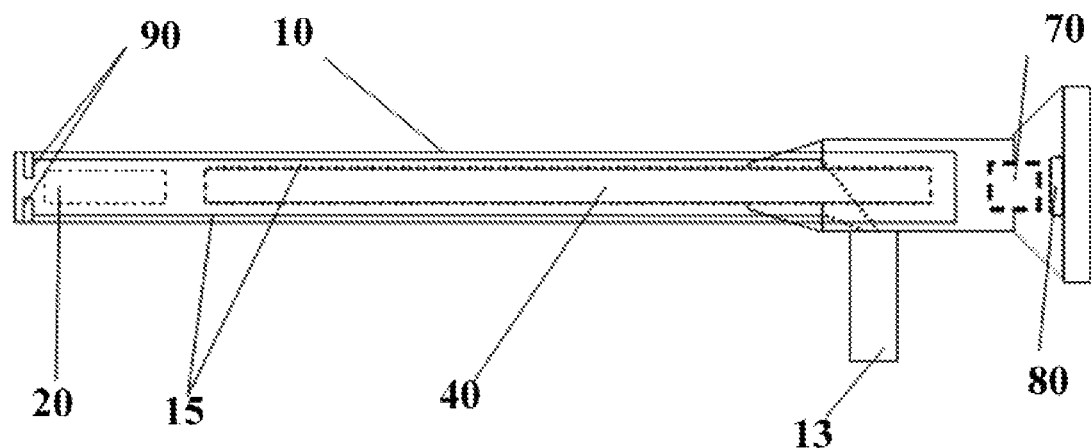
FIG. 4 is a schematic structural sectional view of an inseparable rigid endoscope provided by some embodiments of the present invention.

The embodiment of the present invention provides a detachable rigid endoscope. FIGS. 2, 3 and 4 are sectional views of the rigid endoscope provided by some embodiments of the present invention taken along the axial direction. As illustrated in FIGS. 2, 3 and 4, the rigid endoscope comprises an outer endoscope tube 10 (as these embodiments provide a single-tube rigid endoscope, the outer endoscope tube may be also referred to as endoscope tube), a main endoscope body 12, a LED chip 90, an objective lens group 20, a rod lens group 40 and an eyepiece group 70. The objective lens group 20, the rod lens group 40 and the eyepiece group 70 form an imaging system of the rigid endoscope. For convenient description, one end of the rigid endoscope provided with objective lenses (namely facing an observed object) is referred to as front end, and one end of the rigid endoscope facing the observer is referred to as rear end. The description of other components may also refer to the above terms front end and rear end used for describing orientation.

As can be seen from FIG. 2, the objective lens group 20, the rod lens group 40 and the eyepiece group 70 are sequentially arranged in the endoscope tube 10 in a direction from the front end to the rear end of the endoscope tube 10. The rear end part of the endoscope tube 10 is inserted into the main endoscope body 11. The LED chip is disposed in the front end part of the endoscope tube, so as to provide lighting while viewing. Each of the objective lens group 20, the rod lens group 40 and the eyepiece group 70 may include one or more lenses, so that the observed object can be imaged and observed from the side of the eyepiece. The specific number and the specific shape of the lenses in each lens group are not specifically limited in the embodiment of the present invention and may be randomly designed according to actual demands. For instance, the rod lens group is a part used for image transmission in the imaging system and is, for instance, disposed between the objective lens group and the eyepiece group.

Figure 5:
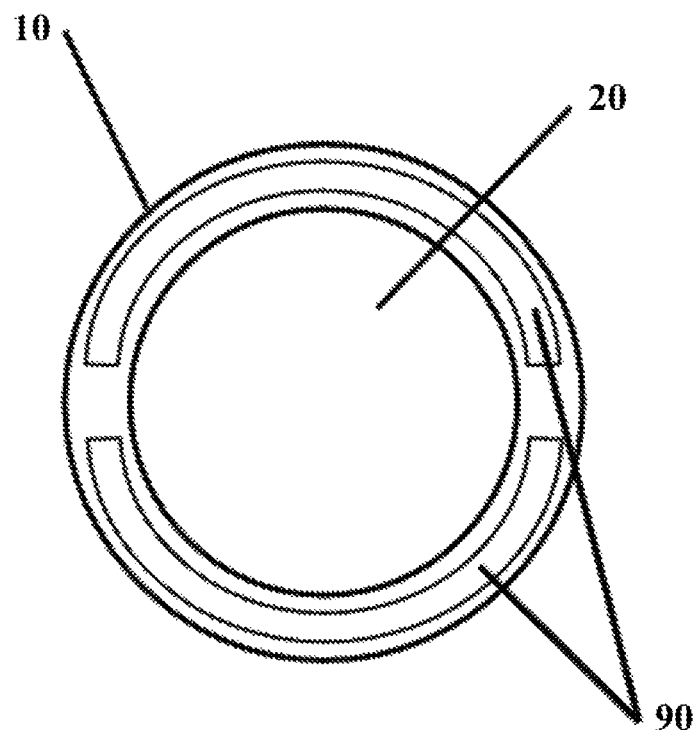
FIG. 5 is a schematic diagram of a front end surface of the endoscope tube of the rigid endoscope provided by some embodiments of the present invention.

In some embodiments, in order to improve the brightness and the uniformity, the LED chip 90 is disposed at the edge of the front end of the objective lens group 20. For instance, the LED chip 90 may be close to the inner wall of the endoscope tube 10. For instance, the LED chip 90 may be an annular LED chip or a plurality of LED chips which are annularly distributed near the inner wall of the endoscope tube 10. For instance, the LED chip 90 may be designed to be an annular chip or a plurality of LED chips arranged in an annular shape or a chip set disposed on a flexible material. FIG. 5 is a schematic end view of a part of the endoscope tube in some embodiments, provided with the LED chip near the front end. As shown in FIG. 5, the annular LED chip 90 is disposed between an inner circle (inner wall) of the endoscope tube 10 and an outer circle (outer wall) of the objective lens 20. That is to say, the LED chip 90 may be disposed in a gap between the endoscope tube 10 and the objective lens 20. However, when high brightness is required, a large-size LED chip is required, and at this point, the LED chip can be disposed at the front end of the objective lens group and may shield partial field, as shown in FIGS. 2, 3 and 4. Therefore, in the case of selecting LED chips, the structure can arrive at a compromise between the brightness and the field size.

Figure 6:
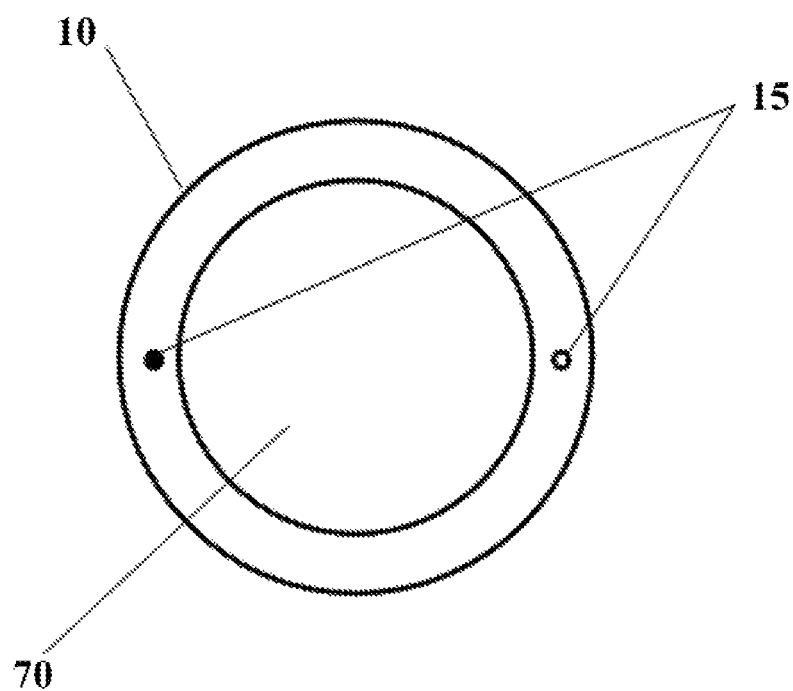
FIG. 6 is a schematic diagram of a rear end surface of the endoscope tube of the rigid endoscope provided by some embodiments of the present invention.

In addition, in order to supply power for the LED chip 90, the rigid endoscope provided by the embodiment of the present invention may further comprise a lead 15 used for supplying power for the LED chip 90. For instance, as shown in FIG. 3 or 4, the lead 15 led out from the LED chip 90 runs through the gap between the inner circle (inner wall) of the endoscope tube 10 and the outer circle (outer wall) of the objective lens group 20 and arrives at the rear end of the endoscope tube 10. FIG. 6 is a schematic diagram of a rear end surface of the endoscope tube of the rigid endoscope provided by the embodiment of the present invention. As can be seen from FIG. 6, the lead 15 is disposed between an outer circle (outer wall) of the eyepiece 70 and the inner circle (inner wall) of the endoscope tube 10, on the rear end part of the endoscope tube.

It should be noted that description is given in the above embodiment by taking the single-tube rigid endoscope as an example, an LED illuminating system provided by the present invention may also be applied in rigid endoscopes in other forms (e.g., a double-tube rigid endoscope).

In some embodiments, an eyeshade 14 is also disposed at the rear end of the main endoscope body of the rigid endoscope, so as to provide convenience for the observer to observe. The specific shape and material of the eyeshade 14 are not specifically limited in the rigid endoscope provided by the embodiment of the present invention.

In some embodiments, in order to conveniently lead the lead 15 out of the main endoscope body 12, a power supply channel 13 is disposed near the eyeshade 14. The power supply channel 13 runs through the tube wall of the main endoscope body 12. The lead 15 is led out from the rear end of the endoscope tube 10, runs through the power supply channel 13, arrives at the outside of the main endoscope body 12, and is communicated with a power source to supply power for the LED chip 90. The power supply channel 13 can protect the lead 15 from being damaged, and meanwhile, can also avoid the lead 15 from obstructing the observer's sight when being led out from the eyeshade 14.

In the embodiment of the present invention, the endoscope tube 10 and the main endoscope body 12 may adopt detachable connection. As shown in FIG. 3, the objective lens group 2, the rod lens group 4 and the eyepiece group 7 are disposed in the endoscope tube 10. The endoscope tube 10 may be a disposable endoscope tube. As the objective lens group, the rod lens group and the eyepiece group may be disposed in the disposable endoscope tube, optical image adjustment (for instance, the cooperative relationship between the lens groups) has been already completed before use, and the endoscope tube is completely sealed and favorable for disinfection. Image adjustment is not required in the use process, so the optical rigid endoscope provided by the embodiment of the present invention can be more conveniently used and more favorable for popularization. As the endoscope tube part is detachable and is a disposable product, cross-infection can be avoided. In addition, as the imaging system is placed in an endoscope tube integral structure (endoscope tube) and the LED chips 90 and the lead 15 are also sealed in the endoscope tube, optical image adjustment has been already completed before use; the endoscope tube is completely sealed and favorable for disinfection; and image adjustment is not required in the use process.

In some embodiments, the lenses in at least one of the objective lens group 20, the rod lens group 40 or the eyepiece group 70 adopt die cast lenses, namely the lenses are made from various optical materials by one-time die casting method. The adopted optical materials include but not limited to transparent resin. For instance, the lenses in the objective lens group 20, the rod lens group 40 and the eyepiece group 70 may be aspheric lenses. In addition, the diameter of the lenses in the objective lens group 20, the rod lens group 40 and the eyepiece group 70 may be roughly equal. As the lenses are formed by die casting method, the cost may be reduced to be a few percent of the cost of the traditional process such as milling, grinding and polishing, cutting and gluing. In addition, aspheric imaging can be realized by the die casting of the lenses, so the imaging quality can be obviously improved compared with the traditional optical glass spherical lenses. The cost of the objective lens group 2, the rod lens group 4, the eyepiece group 7 and the optical fiber made from the traditional optical material, glass, is at least half of the cost of the entire rigid endoscope. Particularly as for the rod lens group 4 with the highest cost, the cost can be greatly reduced if one-time die casting is adopted. Therefore, the rod lens group in the rigid endoscope provided by the embodiment of the present invention may be an integral optical element. The embodiment of the present invention not only can ensure that the imaging quality of the built-in imaging system can be greatly improved but also can greatly reduce the production cost as the lenses are formed by die casting method.

The material of the endoscope tube 10, taken as a key part for entering the human body, can meet medical standards and have certain strength and be difficult to bend. Therefore, in some embodiments, stainless steel tube is selected as the material of the outer endoscope tube 10. However, the material of the outer endoscope tube of the rigid endoscope provided by the present invention is not limited to stainless steel.

As described above, on the premise of adopting single-tube endoscope, LED illumination and one-time die casting of aspheric lenses, the rigid endoscope may be manufactured to be detachable in the embodiment of the present invention, namely the endoscope tube 10 and the main endoscope body 12 may be separable, so the endoscope tube and the imaging system in the endoscope tube and the LED chip 90 become disposable products. As shown in FIG. 3, due to adoption of detachable connection, the endoscope tube can be conveniently connected or separated on site, so the endoscope tube part become disposable consumable and the main endoscope body 12 is repeatedly used. Therefore, the optical rigid endoscope provided by the present invention may be massively used, so the cost can be greatly saved for hospitals and patients. As the endoscope tube part is detachable and is a disposable product, cross-infection can be avoided.

In addition, as shown in FIG. 4, the embodiment of the present invention further provides an inseparable rigid endoscope, which comprises an endoscope tube 10, a LED chip 90, a lead 15, an imaging system including an objective lens group 20, a rod lens group 40 and an eyepiece group 70, and a rear protection plate 80. The lead 15 led out from the LED chip 90 runs through a communicating gap and is connected to the rear end of the endoscope tube. In order to conveniently lead the lead 15 out of a main endoscope body 12, a power supply channel 13 is disposed near an eyeshade 14 and runs through the tube wall of the main endoscope body 12, and the lead 15 is led out from the rear end of the endoscope tube 10, runs through the power supply channel 13, arrives at the outside of the main endoscope body 12, and is communicated with a power source to supply power for the LED chip 90. The power supply channel 13 can protect the lead 15 from being damaged, and meanwhile, can also avoid the lead 15 from obstructing the observer's sight when being led out from the eyeshade. In the inseparable rigid endoscope, the eyepiece group 70 is disposed in the main endoscope body 12. Other parts may refer to the detachable rigid endoscope as described above, and no further description will be given to repeated parts. When eyepieces are disposed in the main endoscope body 12, the lead is led into the power supply channel 13 from a gap between the endoscope tube 10 and the rod lens group 40, on the rear end part of the endoscope tube, as shown in FIG. 4. Of course, as for the inseparable rigid endoscope, the eyepiece group 70 may also be disposed in the endoscope tube 10. The structure may refer to the description in the above embodiment.

In the rigid endoscope provided by any foregoing embodiment, the main endoscope body 12 mainly has the function of clamping one end of the endoscope tube, so as to be favorable for the operation of the endoscope tube. In addition, the main endoscope body is also taken as a lead-out position of the lead for supplying power for the LED chip, and a window for observation. The specific shape of the main endoscope body is not specifically limited in the embodiment of the present invention.

The embodiment of the present invention adopts the LED chips 90 for lighting, has small volume, and is convenient in mounting. In addition, as the LED chip adopts annular LED chip or annular shape formed by a plurality of LED chips, the cost is low. Compared with the traditional optical fiber lighting, the cost of the illuminating system of the optical rigid endoscope provided by the embodiment of the present invention is also reduced. The lighting angle of the LED chips 90 is also large. As high-power LED chips can be selected, formed images can be clearer.

Compared with the traditional rigid endoscope, the cost of the method of adopting single-tube design, LED front-end lighting and one-time die casting of aspheric lenses is greatly reduced and can be reduced to one-tenth to one-twentieth. Meanwhile, after the LED chip replaces the optical fiber for lighting, the brightness uniformity is obviously improved; the contrast is improved; and the optical transfer function (OTF) is increased, so the resolution is improved.

Figure 7:
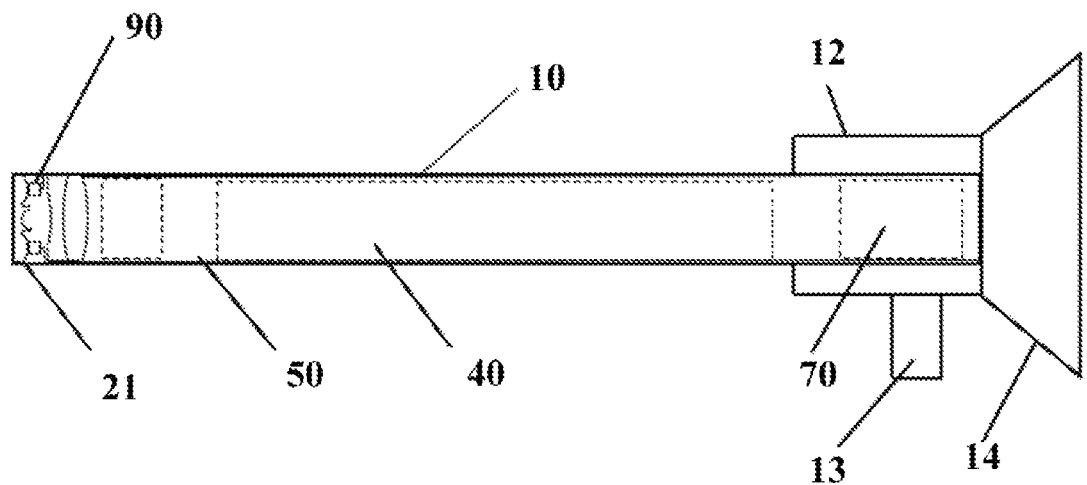
FIG. 7 is a schematic structural sectional view of a rigid endoscope provided by some embodiments of the present invention.

Some embodiments of the present invention further provide a rigid endoscope adopting LED chip for lighting, which, as shown in FIG. 7, comprises a main endoscope body 12, an endoscope tube 10 and an imaging system including an objective lens group 20, a rod lens group 40 and an eyepiece group 70. The objective lens group 20 includes a first objective lens 21 and a second objective lens 22. The first objective lens 21 and the second objective lens 22 are sequentially arranged in the endoscope tube 10 in the direction from the front end to the rear end. In these embodiments, a LED chip 90 is also arranged. The difference from the above embodiments is that the LED chip 90 is mounted between the first objective lens 21 and the second objective lens 22 and disposed at the edge of the rear end of the first objective lens 21. The setting means ensures the required angle of field and the imaging resolution. Compared with the proposal that the LED chip is disposed at the front end of the first objective lens 21, field shielding can be avoided, and the resolution can be improved. In addition, the rigid endoscope in these embodiments may comprise components such as the lead 15 and the power supply channel 13 as similar to the above embodiments. The lead 15 led out from the LED chip 90 runs through a communicating gap, arrives at the rear end of the endoscope tube 10, runs through the power supply channel 13, and is led out of the main endoscope body 12. As shown in FIG. 7, in these embodiments, a spacer 50 may be also arranged. For instance, the spacer 50 may be disposed between the eyepiece group and the rod lens group and/or between the objective lens group and the rod lens group, and may also be disposed at other required positions. The spacer 50 may be in hollow shape for light to pass through. The spacer 50 in these embodiments may also be applied in the foregoing embodiments.

Figure 8:
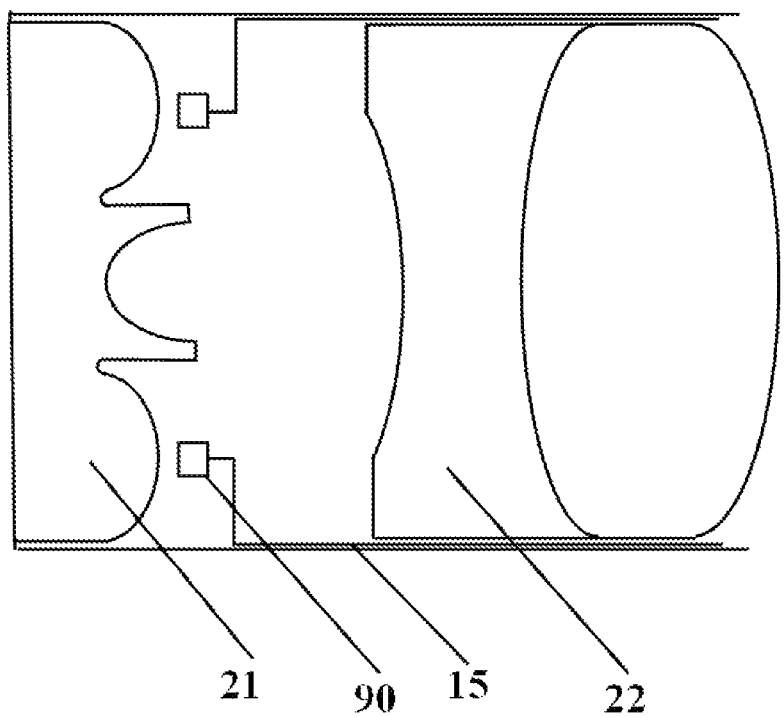
FIG. 8 is a schematic partial sectional view of a rigid endoscope provided by some embodiments of the present invention.
Figure 9:
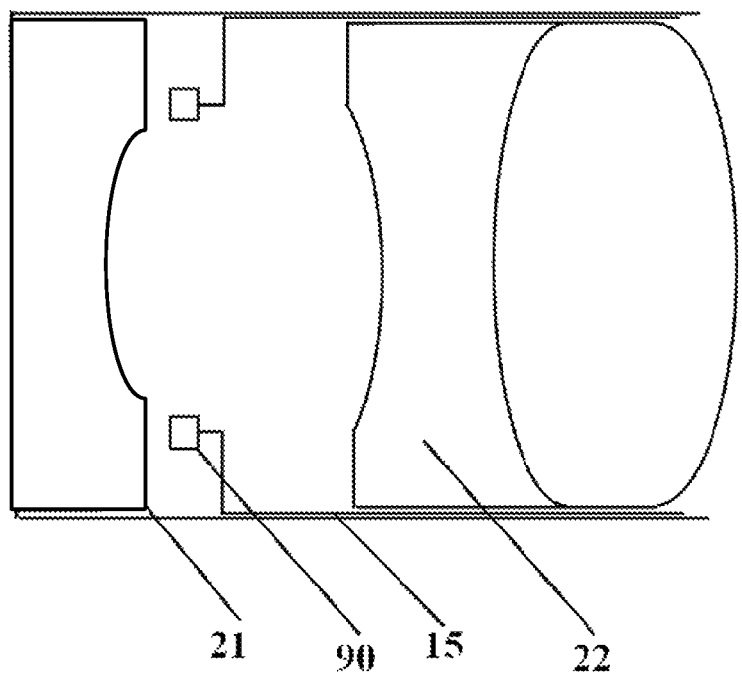
FIG. 9 is a schematic partial sectional view of a rigid endoscope provided by some embodiments of the present invention.

As for a rigid endoscope with small diameter, the relationship between the size of the LED chip and the maximum optical power is a current technical bottleneck. In the current market, chips with minimum size have low optical power, and although the chips may be disposed at the most significant end (the front end of the objective lens), the chips will also shield the imaging field. When the LED power is increased, the size of the LED chips will also be increased, and the field shielding range will also be increased. In these embodiments of the present invention, as shown in FIGS. 8 and 9, the first objective lens 21 may include a central portion, of which the rear end surface is designed to be a concave surface, and an edge portion disposed at the periphery of the central portion. As the central part of which the rear end surface of the objective lens is designed to be the concave surface is actually used for imaging, the LED chip will not shield the field when disposed on the edge portion at the periphery of an imaging area.

In addition, the LED chip is disposed on the edge portion of the first objective lens 21. The propagation of light emitted from the LED chip to the observed object can be better controlled by setting of the optical properties of the edge portion. The LED luminous angle is about 120°-140°, and the angle of field of the endoscope is about 70°-80°, so the LED luminous angle is far greater than the angle of field, and hence the optical energy is not fully utilized. As shown in FIG. 8, the edge portion of the first objective lens 21 is designed to be a curved surface protruded towards the rear end, so the light emitted by the LEDs can be converged and the luminous angle of the LEDs can be converged. Therefore, the light emitted by the LEDs can be more fully utilized within the angle of field of the endoscope, so the brightness can be improved and the influence on the imaging system can be avoided. A central part on the back (rear end surface) of the first lens is a concave surface and is used for imaging.

For instance, the embodiment of the present invention is also not limited to design the edge portion of the first objective lens to be a curved surface, and the edge portion of the first objective lens 21 may be designed to be a curved surface or a plane favorable to propagate light towards the front end and inhibit stray light. As shown in FIG. 9, the rear end surface of the edge portion of the first objective lens 21 is a plane. In addition, the rear end surface of the edge portion of the first objective lens 21 may be also designed to be any other required surface.

For instance, as shown in FIGS. 8 and 9, the front end surface of the first objective lens 21 is a plane. Therefore, the first objective lens 21 may be also taken as a forefront protection plate of the rigid endoscope. In this case, the front protection plate is not required to be independently arranged, so the cost can be reduced. For instance, the first objective lens is disposed at the most significant end of the endoscope tube 10.

In some embodiments, the LED chip 90 is a white-light LED chips, but the embodiment of the present invention is not limited thereto. The endoscope tube 10 is made from stainless steel materials, but the embodiment of the present invention is not limited thereto.

Some other embodiments of the present invention provide a rigid endoscope, which comprises: an endoscope tube, an objective lens group and a rod lens group, wherein the objective lens group and the rod lens group are disposed in the endoscope tube and arranged in a direction from the front end to the rear end of the endoscope tube; and at least one of the objective lens group or the rod lens group adopts die cast lenses.

In some examples, the rigid endoscope further comprises a main endoscope body and an eyepiece group; the rear end of the endoscope tube is connected to the main endoscope body; the eyepiece group is disposed in the endoscope tube and at the rear end of the rod lens group; or the eyepiece group is disposed in the main endoscope body.

In some examples, the eyepiece group adopts die cast lenses.

In some examples, the lenses in at least one of the objective lens group, the rod lens group or the eyepiece group adopt aspheric lens design.

In some examples, the rod lens group is an integral optical element.

Some other embodiments of the present invention further provide a rigid endoscope, which comprises: an endoscope tube, an objective lens group, a rod lens group and an eyepiece group, wherein the objective lens group, the rod lens group and the eyepiece group are sequentially arranged in the endoscope tube in a direction from the front end to the rear end of the endoscope tube; and at least one of the objective lens group, the rod lens group or the eyepiece group adopts die cast lenses.

In some examples, the lenses in at least one of the objective lens group, the rod lens group or the eyepiece group adopt aspheric lens design.

In some examples, other structures may refer to the description in the above embodiments. For instance, the illuminating system of the rigid endoscope may refer to the foregoing LED illuminating system, but not limited thereto, other illuminating systems may be also adopted. For instance, the connection of the rear end of the endoscope tube and the main endoscope body in these examples may also be detachable connection or inseparable connection.

In addition, the structures in the embodiments of the present invention may be mutually combined and replaced. For instance, the die cast lenses, the aspheric lenses, the LED illuminating system and the single-tube design may be applied in the embodiments independently or in conjunction with each other. No further description will be given here.

The rigid endoscope provided by the embodiment of the present invention at least has one of the following advantages.

As all of the objective lens group, the rod lens group and the eyepiece group in the optical rigid endoscope provided by the embodiment of the present invention adopt one-time die cast lenses, compared with the traditional process such as milling, grinding and polishing, cutting and gluing, the material cost and the production cost are greatly reduced.

As the rigid endoscope provided by the embodiment of the present invention adopts die cast lenses, aspheric imaging can be realized. As all the lenses have roughly consistent diameter and may be assembled into one endoscope tube, compared with the traditional glass spherical lens, the imaging quality is obviously improved, and the number of lenses can be also reduced, so the cost can be greatly reduced.

As the rigid endoscope provided by the embodiment of the present invention adopts single-tube design, the diameter of optical elements is increased, so the imaging resolution can be obviously improved, and film coating and assembly can be more convenient.

The rigid endoscope provided by the embodiment of the present invention adopts LED lighting. As the cost of the LED chips is very low, the cost of the optical rigid endoscope can be reduced. The chip set is designed to be continuous and bendable or an annular shape is formed by chips or the chips are placed on the flexible material, so the LED chips can be adapted to rigid endoscopes with different diameters and different angles of field and have universality.

As the rigid endoscope provided by the embodiment of the present invention adopts the case of placing the LED chips at the front end of the endoscope tube, the lighting angle can be increased and the uniformity can be improved; the imaging resolution can be finally improved; and the energy can be also saved.

The rigid endoscope provided by the embodiment of the present invention adopts separable design: as the objective lens group, the rod lens group and the eyepiece group are disposed in the disposable endoscope tube, optical image adjustment has been completed before use; the endoscope tube is completely sealed and favorable for disinfection; image adjustment is not required in the use process; and hence the optical rigid endoscope provided by the embodiment of the present invention can be more conveniently used and more favorable for popularization. The endoscope tube part in the embodiment of the present invention becomes disposable consumable; the rear main endoscope body part can be repeatedly used; and together with the subsequent low-price imaging system, the rigid endoscope can be massively used in outpatient service, so the cost can be greatly saved for hospitals and patients. As the endoscope tube part is detachable and is a disposable product, cross-infection can be avoided. The disposable detachable ultrahigh-image-quality rigid endoscope with extremely low cost can be realized. Ultrahigh image quality refers to ultrahigh resolution which is obviously higher than high resolution, basically elimination of distortion, large angle of field, elimination of field curvature, and high depth of field.

The rigid endoscope provided by the embodiment of the present invention can also adopt inseparable design: the objective lens group, the rod lens group and the eyepiece group are still disposed in the single endoscope tube, and the main endoscope body adopts one-time die casting materials, so the disposable ultrahigh-image-quality rigid endoscope with extremely low cost can be realized.

In the rigid endoscope provided by the embodiment, the LED lighting has low cost, and the LED chip is disposed at the edge of the rear end of the first objective lens, so the required angle of field and the imaging resolution can be guaranteed. Compared with the proposal that the LED chip is disposed at the front end of the first objective lens, field shielding can be avoided, so the resolution can be improved.

In the rigid endoscope provided by the embodiment of the present invention, the rear end surface at the edge of the first objective lens is designed to be a curved surface or a plane favorable to propagate light towards the front end and inhibit stray light, so light of LED patches with overlarge luminous angle can be converged, and hence the influence on the imaging system can be avoided, and the brightness can be enhanced.

One front protection plate can be reduced in the rigid endoscope design of the embodiment of the present invention, so the cost can be reduced considering from the material and the mounting angle.

The foregoing is only the preferred embodiments of the present invention and not intended to limit the scope of protection of the present invention. The scope of protection of the present invention should be defined by the appended claims.

The application claims priority to the Chinese patent applications No. 201520532348.5 and No. 201520532346.6, filed Jul. 22, 2015, the disclosure of which is incorporated herein by reference as part of the application.

The invention claimed is:
1. A rigid endoscope, comprising:
an endoscope tube;
an objective lens group;
a rod lens group;
an eyepiece group;
a light-emitting diode (LED) chip,
  wherein the LED chip has an annular shape; and
a lead, wherein:
  the objective lens group and the rod lens group are disposed in the endoscope tube and arranged in a direction from a front end to a rear end of the endoscope tube,
  the eyepiece group is disposed in the endoscope tube and at a rear end of the rod lens group,
  the LED chip is mounted at the front end of the endoscope tube,
  the lead is led out from the LED chip, runs through a gap between an inner circle of the endoscope tube and an outer circle of the objective lens group, and arrives at the rear end of the endoscope tube,
  the rigid endoscope is a single-tube rigid endoscope,
  the LED chip is disposed at an edge portion, which is close to the inner circle of the endoscope tube, of the objective lens group, and
  in the direction from the front end to the rear end of the endoscope tube, an entirety of the LED chip is overlapped with each of the objective lens group, the rod lens group, and the eyepiece group.

2. The rigid endoscope according to claim 1, wherein the objective lens group, the rod lens group, and the eyepiece group are sealed into the endoscope tube.

3. The rigid endoscope according to claim 1, wherein the objective lens group, the rod lens group, the eyepiece group, the LED chip and the lead are sealed into the endoscope tube.

4. The rigid endoscope according to claim 1, wherein:
the objective lens group includes a first objective lens and a second objective lens;
the first objective lens and the second objective lens are sequentially arranged in the direction from the front end to the rear end of the endoscope tube; and
the LED chip is mounted between the first objective lens and the second objective lens and disposed at the edge of a rear end of the first objective lens.

5. The rigid endoscope according to claim 4, wherein:
the first objective lens includes a central portion, of which a rear end surface is set to be a concave surface, and an edge portion disposed at the periphery of the central portion; and
a rear end surface of the edge portion is a curved surface or a plane, so that light emitted from the LED chip can propagate towards the front end and stray light can be suppressed.

6. The rigid endoscope according to claim 5, wherein the rear end surface of the edge portion of the first objective lens is a curved surface protruding towards the rear end of the endoscope tube.

7. The rigid endoscope according to claim 1, wherein the lenses of at least one of the objective lens group, the rod lens group or the eyepiece group adopt aspheric lens design and have roughly equal diameter.

8. The rigid endoscope according to claim 1, wherein at least one of the objective lens group, the rod lens group or the eyepiece group adopts die cast lens.

9. The rigid endoscope according to claim 1, further comprising a main endoscope body,
wherein the endoscope tube and the main endoscope body adopt detachable assembled connection structure or inseparable integral structure.

10. The rigid endoscope according to claim 9, further comprising a power supply channel running through a tube wall of the main endoscope body and the endoscope tube; and
wherein a rear end of the lead is led out from the power supply channel to the outside of the main endoscope body.

11. A rigid endoscope, comprising:
an endoscope tube;
an objective lens group;
a light-emitting diode (LED) chip,
  wherein the LED chip has an annular shape;
a rod lens group, wherein:
  the objective lens group and the rod lens group are disposed in the endoscope tube and arranged in a direction from a front end to a rear end of the endoscope tube,
  at least one of the objective lens group or the rod lens group adopts die cast lens, and
  the rigid endoscope is a single-tube rigid endoscope; and
a lead between an inner circle of the endoscope tube and an outer circle of the objective lens group, and between the inner circle of the endoscope tube and an outer circle of the rod lens group, wherein the LED chip is disposed at an edge portion, which is close to the inner circle of the endoscope tube, of the objective lens group, and in the direction from the front end to the rear end of the endoscope tube, an entirety of the LED chip is overlapped with each of the objective lens group and the rod lens group.

12. The rigid endoscope according to claim 11, further comprising a main endoscope body and an eyepiece group, wherein:

the rear end of the endoscope tube is connected to the main endoscope body;

the eyepiece group is disposed in the endoscope tube and at the rear end of the rod lens group; or the eyepiece group is disposed in the main endoscope body.

13. The rigid endoscope according to claim 12, wherein the lenses of at least one of the objective lens group, the rod lens group or the eyepiece group adopt aspheric lens design.

14. The rigid endoscope according to claim 11, wherein the eyepiece group adopts die cast lens.

15. The rigid endoscope according to claim 11, wherein the rod lens group is an integral optical element.

* * * * *